Figure 5:
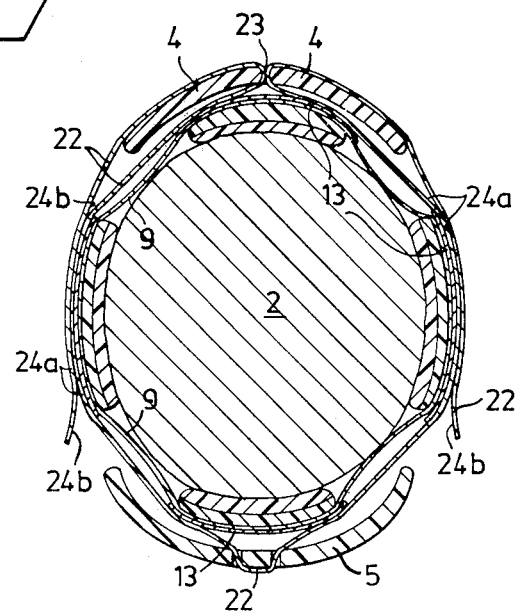

United States Patent [19]

Marsh et al.

[11] 4,268,922

[45] May 26, 1981

[54] PREFABRICATABLE, ARTIFICIAL LOWER LEG

[75] Inventors: Gunnar Marsh, Karlskrona; Christer B. Olander, Lyckeby, both of Sweden

[73] Assignee: Landstingens Inköpscentral, Lic, ekonomisk förening, Solna, Sweden

[21] Appl. No.: 82,757

[22] Filed: Oct. 9, 1979

[30] Foreign Application Priority Data

Oct. 12, 1978 [SE] Sweden .................................. 7810653

[51] Int. Cl.³ .............................................. A61F 1/08
[52] U.S. Cl. ................................................. 3/21; 3/2; 128/89 R
[58] Field of Search .......................... 3/2, 16, 17 R, 21; 128/80 F, 88, 89 R

[56] References Cited

U.S. PATENT DOCUMENTS

| 21,289 | 8/1858 | Wilcox ...................................... 3/17 R |
| 143,537 | 10/1873 | Silberschmidt ...................... 128/89 R |
| 1,211,222 | 1/1917 | Pilling et al. ............................ 3/17 R |
| 1,572,318 | 2/1926 | Scully ...................................... 3/17 R X |
| 3,545,046 | 12/1970 | Colley ..................................... 3/17 R X |
| 3,701,349 | 10/1972 | Larson ................................. 128/89 R X |
| 4,128,903 | 12/1978 | Marsh et al. ............................ 3/21 X |

FOREIGN PATENT DOCUMENTS 10095 of 1915 United Kingdom ............................. 3/2
1086560 10/1967 United Kingdom ............................. 3/2

*Primary Examiner*—Clifford D. Crowder
*Attorney, Agent, or Firm*—Cushman, Darby & Cushman

[57] ABSTRACT

A prosthetic lower leg or prosthesis comprising two plates mutually connected downwardly and to a prosthetic foot, while upwards they are enlarged into circular coacting sleeve halves, together forming an adjustable carrying sleeve. By means of an annular tensioning device the sleeve can be tightened round the leg stump which can be fixed laterally in the prosthesis by special tension straps between the plates, as well as longitudinally relative to the prosthesis by means of a strap which is attached to the carrying sleeve and tightenably laid round the leg stump in a loop. The weight on the leg stump is substantially transferred to the prosthesis via bands attached to the outside of a stocking on the stump and extend up over the edge of the carrying sleeve and from there down on the outside of the sleeve where the free ends of the bands are anchored.

8 Claims, 6 Drawing Figures

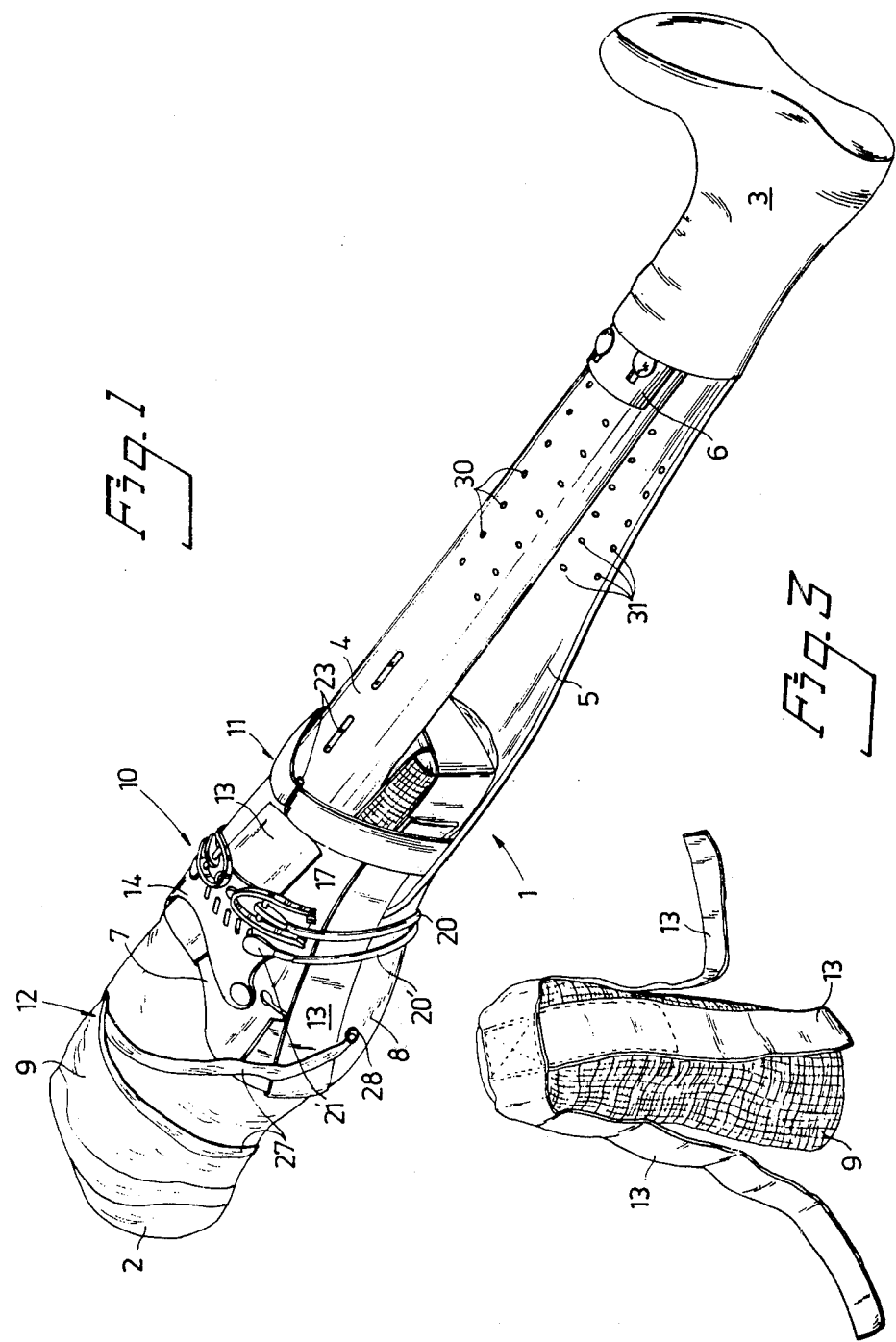

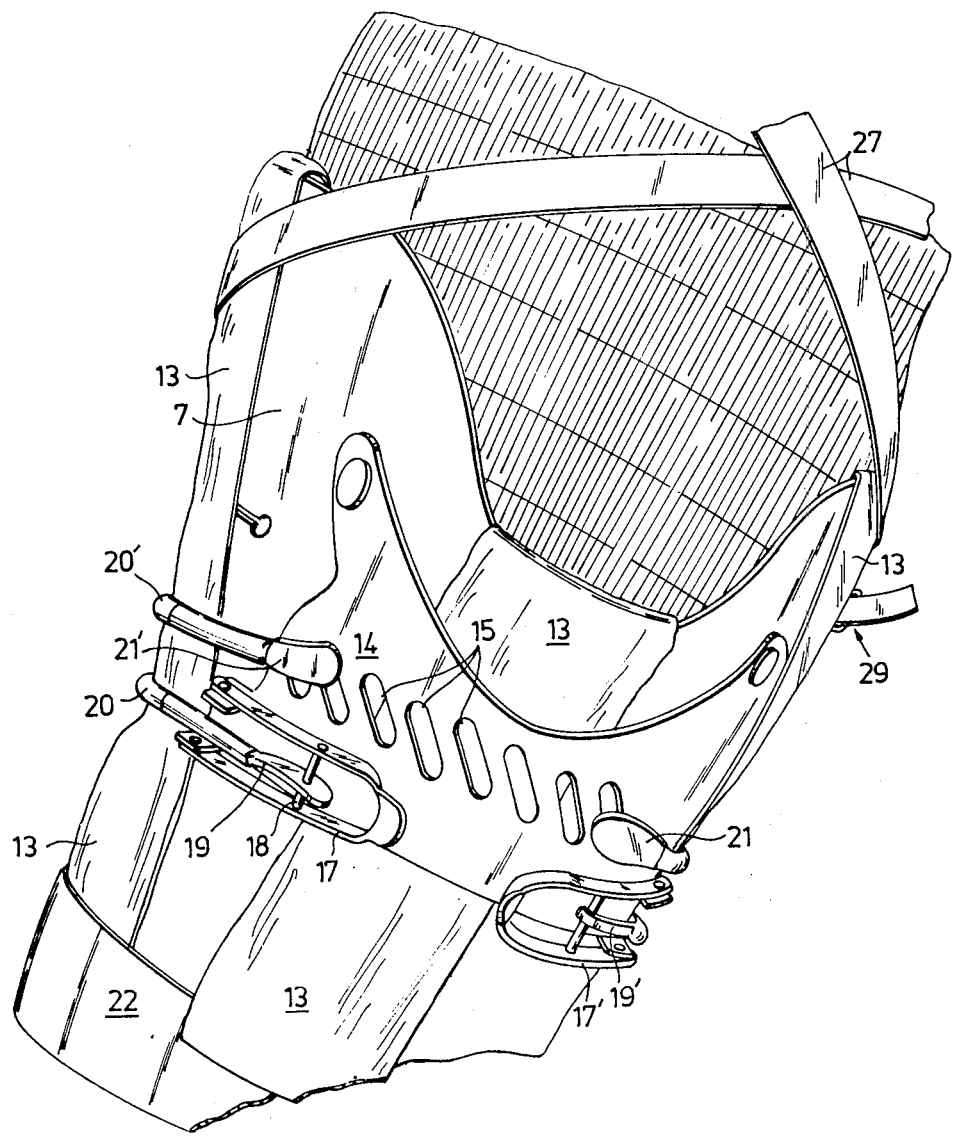

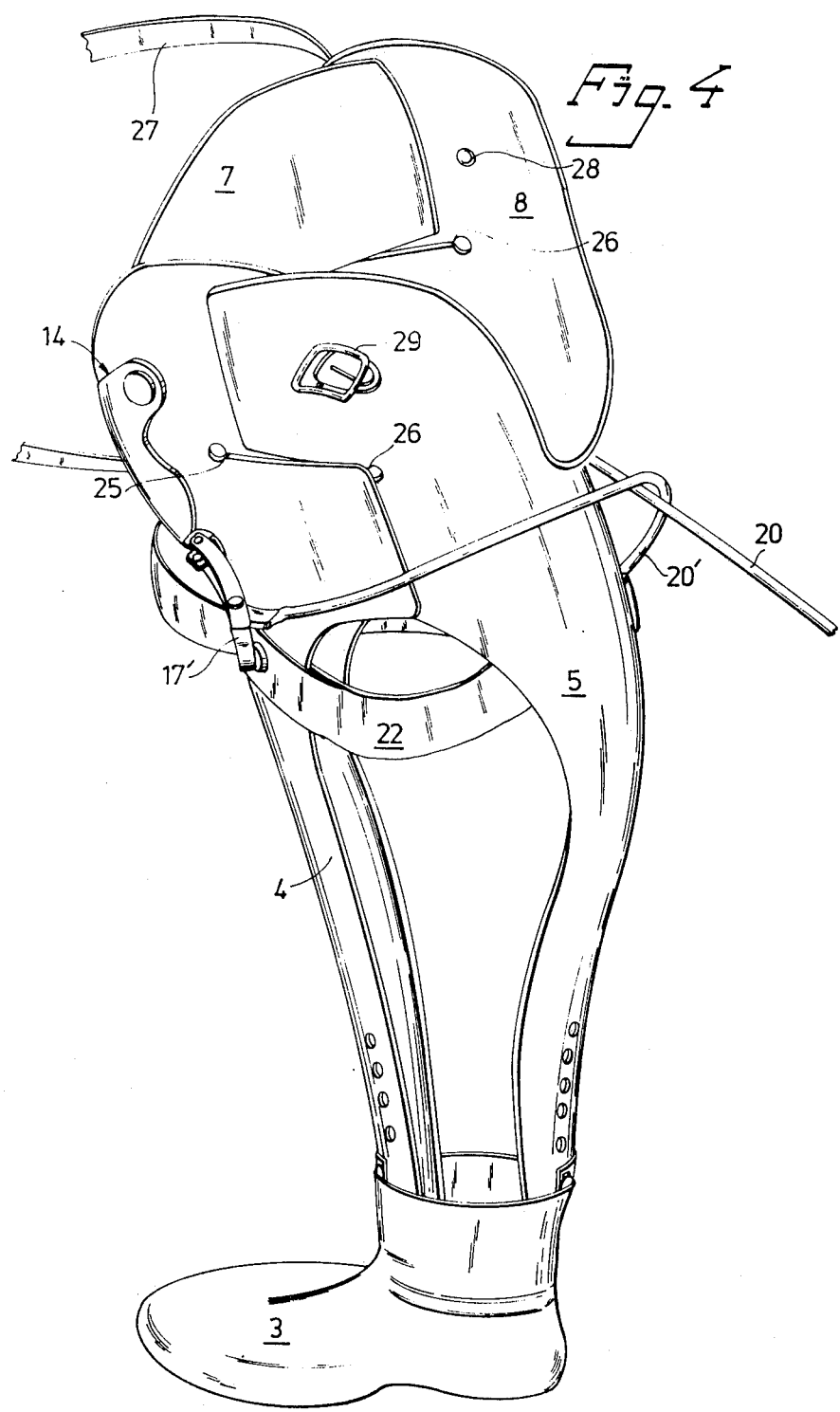

PREFABRICATABLE, ARTIFICIAL LOWER LEG

The present invention relates to a prosthesis or artificial limb for replacing an amputated lower leg.

In practice, it has so far been necessary especially to manufacture a lower leg prosthesis individually for the person needing one to replace an amputated lower leg. Such manufacture has had to take place more or less by hand, several fittings usually being needed in conjunction with producing the prosthesis, so that it will fit acceptably to the leg stump. Both manufacture and fitting have required especially trained staff and have also been time-consuming, which has made such prostheses expensive to prepare.

The object of the present invention is therefore to produce a new type of lower leg prosthesis which can be prefabricated in series and which only needs to be manufactured in a single, or some few standard sizes, although it is usable for practically anyone needing such prosthesis. The prosthesis also is to be quickly and easily adjustable to the patient's leg stump, without requiring any previous modification thereof. Fitting and attachment of the prosthesis to the leg stump also is to be simple to carry out, and should not require especially trained staff.

The problem forming the background of the invention is thus the provision of an artificial limb or prosthesis of the kind given in the introduction, which is individually adjustable to the leg stump of the wearer in a simple mode, as well as being easy to fasten to the leg stump, while taking into consideration the bodily size of the wearer.

In accordance with the invention, the problem is solved by the prosthesis comprising a front plate with a back plate opposite to it, these being rigidly attached to each other at their lower ends and preferably articulatedly connected to a prosthetic foot, each plate being upwardly formed into a sleeve portion. These sleeve portions are adapted for being mutually connected in circular configuration upwardly, to form a bowl-like enlarged carrying sleeve permitting the entry of a leg stump with a supporting stocking drawn over it, after the upper portions of the plates, and thereby to a certain extent the supporting sleeve portions have been pulled apart against their spring bias, subsequent to which the sleeve portions are allowed to flex back again towards each other and surround the stump just below the knee. The prosthesis further has devices adapted for tightening the carrying sleeve portions firmly about the stump, for lateral adjustment of the prosthesis relative to the stump, and longitudinal fixation of the prosthesis relative to the stump, here being supporting bands attached to the outside of the supporting stocking, extending upwards along the stocking and the stump contained by it, and intended to have their free ends folded over the edge of the carrying sleeve to extend downwards against it for being clamped tight against the outside of the carrying sleeve portions.

The length of the prosthesis, i.e. the length of the plates, can be adjusted with respect to the wearer by making the plates relatively long and then shortening them at the bottom as required. The plates can be rigidly attached to each other at their lower ends, either by their being attached to a common jointing piece to which the prosthetic foot is then attached, or by having the plates merging into a common lower portion at a suitable distance below their sleeve portions, with the prosthetic foot attached to said common lower portion. In the latter case, both plates are thus made integral with each other and with the common lower portion, i.e. the plates form front and back prosthesis portions extending upwards from the common lower portion.

In order to simplify the attachment of the prosthetic foot, the plates can suitably be provided from the start with longitudinal rows of fixing holes for the common jointing portion or the prosthetic foot.

To a substantial extent, the weight of the patient or wearer on the stump is transferred therefrom to the prosthesis via the supporting bands attached to the outside of the supporting stocking. These bands extend upwards along the stocking and are taken downwardly over the edges of the carrying sleeves for fastening on the outside of the carrying sleeve portions.

The device for tightening the carrying sleeve portions can suitably comprise a fastening plate attached to the front face of the sleeve portion of the front plate. This fastening plate is provided with engagement holes and tensioning levers mounted pivotably at its ends. One end of a tension cable is pivotably attached to each tensioning lever, the cable extending therefrom backwards in a loop around the supporting sleeve, the other end of the cable having hook means enabling the cable to be anchored in one of the engagement holes. When each tensioning lever is swung into its locked tensioning position, it thus causes the associated cable to tighten around the carrying sleeve, thereby clamping the sleeve around the leg stump. The stump is thus fixed and is prevented from swivelling backwards and forwards in the prosthesis.

The lateral adjustment of the stump to a desired angle relative the prosthesis is carried out with a device particularly intended for this purpose. This device can, for example, consist of tensioning straps arranged below the carrying sleeve and tightenable against opposite sides of the leg stump provided with the supporting stocking, said straps extending between the back and front plates, with an adjustable length between the plates. The fixation of the tensioning straps in a desired tensioning position can take place very quickly and simply, e.g. by the straps being provided with Velcro ® tape at suitable places. In a pulled-up position, each tensioning strap can thus extend from a starting place at the back plate, over its side of the supporting stocking (on the leg stump), out through an opening in the front plate, pulled back against the side of the prosthesis and stump, and fixed there by means of the Velcro tape with its free end against the tensioned portion.

For mutual guidance of the sleeve portions forming a circular configuration, the prosthesis can be made such that the backwardly directed side portions of the front plate sleeve portion and/or the forwardly directing side portions of the back plate sleeve portion have substantially horizontal slits separating the respective side portion in at least two tongues enabling the sleeve portions to be pushed together by the respective tongue being glidably displaceable on the side portion of the adjacent sleeve portion.

Alternatively, it is conceivable for the sleeve portion of one plate to have projections, e.g. in the form of projecting tongues, which are displaceably accommodated in recesses, slots or guides in the other sleeve portion.

When the prosthetic foot does not bear against a substructure, e.g. a floor or the ground, which happens intermittently when the person wearing this prosthesis walks, the latter must naturally be prevented from loosening from the leg stump. This is catered for by the device for fixing the prosthesis longitudinally relative to the stump. This device can be such that it comprises attachments fixed to opposite sides of either sleeve portion, there being provided between said attachments a strap or belt which is adjustably tensionable in the form of a loop going upwards, and laid round the leg stump such that at least the greater portion of the loop encircles the stump in the region above the knee.

To avoid the mutual interplay of forces between the stump and the portions, including the supporting bands, associated with the prosthesis being too concentrated to particular surface areas on the leg stump, it is suitable to have elastic spacers placed between the inside of the supporting stocking and the stump. Each of these spacers can consist of webs comprising two layers, one above the other, one being softer and facing towards the stump, while the other, harder layer faces towards the inside of the stocking. The spacers, which are thus placed against the inside of the stocking, are preferably placed directly opposite to the supporting bands going along the outside of the stocking.

In a preferred embodiment of the prosthesis, the supporting bands are tightened against the outside of the carrying sleeve portions by means of the tension cables. Instead, it is also naturally quite possible to anchor or clamp the supporting bands or carrying straps on the outside of the carrying sleeve with the aid of special buckles, fastening eyes or the like on the outside of the sleeve portions, but by utilizing the tension cables for retaining the bands or straps a simpler structure is achieved.

Figure 6:
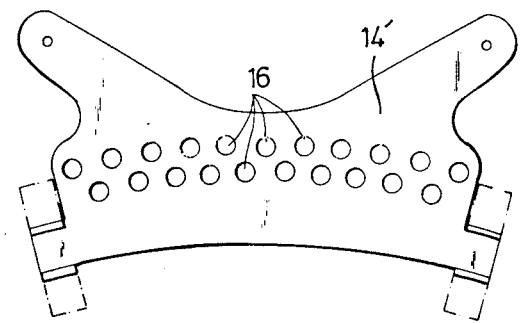

The invention will now be described in detail with the help of an embodiment of the prosthesis illustrated on the appended drawings. On the drawings, FIG. 1 is a perspective view of a portion of a leg stump provided with a prosthesis in accordance with the invention, FIG. 2 illustrates to a larger scale a portion of the prosthesis according to FIG. 1, FIG. 3 is a perspective view of a leg stump (not shown) with a supporting stocking pulled over it, FIG. 4 is a perspective view of the prosthesis before it is applied to the leg stump, FIG. 5 illustrates very schematically a conceived cross section through the prosthesis applied to a leg stump, it being apparent from the figure how the tension straps can be arranged in a fixed position, and, finally, FIG. 6 illustrates, in a developed front view, a second embodiment of the attachment plate provided with two rows of circular attachment holes for the hooking means of the tension cables.

A prosthesis, generally designated 1, is illustrated in FIG. 1 in a fixed position on an only partially shown leg stump 2. Downwardly, i.e. at the foot end, this prosthesis is provided with a prosthetic foot 3 which can be articulatedly or unarticulatedly joined to the plates of the prosthesis. The latter comprises a front plate 4 and a back plate 5 downwardly rigidly connected to each other via a common connecting piece 6 on which is attached the prosthetic foot 3. Upwardly, i.e. at the end of the prosthesis accommodating the stump 2, each of the plates 4,5 are formed into a sleeve half 7 and 8, respectively, of which the half 7 of the front sleeve 4 is most clearly apparent in FIG. 1, while only a side portion of the half 8 of the back plate 5 can be seen in this figure. The sleeve halves 7,8 come against each other to form an upwardly enlarged circular support sleeve in which the leg stump 2 with its supporting stocking 9 is accommodated. When the prosthesis is to be mounted on the stump 2 with its supporting stocking, the upper portions of the plates 4,5 are pulled apart so that the sleeve halves 7,8 are thereby pulled apart sufficiently for the stump to be inserted in the carrying sleeve. The plates are subsequently allowed to spring back towards each other so that their sleeve halves surround the stump just above the knee. The halves 7,8 are then tightened to a firm grip around the stump with the aid of a device generally designated 10 which will be described in detail with reference to FIG. 2. Positioning the stump laterally relative to the prosthesis is done by means of a special device generally denoted 11 and longitudinal fixation of the prosthesis relative to the stump is done by means of a device generally denoted 12.

Four supporting bands 13 (see FIG. 3) are sewn onto the outside of the supporting stocking 9 drawn onto the stump 2, these bands extending upwards along the stocking and (when the stump has been inserted in the prosthesis) have their free ends folded downwards over the upper edge of the carrying sleeve, for tightening against the outside of the sleeve halves.

Turning now to FIG. 2, the device for tightening the carrying sleeve halves will be described in detail. The figure shows how an attachment or fastening plate 14, associated with this device, is riveted to the sleeve half 7 of the front plate 4 and is provided with a transverse row of engagement perforations 15, in this embodiment consisting of a set of inclined, mutually parallel, elongate holes, but could just as well be one or more rows of circular holes 16, e.g. as illustrated in FIG. 6, which also illustrates an alternative embodiment of the fastening plate denoted by 14'. At each end of the fastening plate 14, there is a tensioning means in the form of a pivotably mounted U-shaped tensioning arm 17, between the legs of which there is journalling pin 18 for a cable eye 19. Thus, on the pin 18 associated with each tensioning arm 17 there is anchored a tension cable 20 by means of the cable eye 19, the cable extending backwards from the arm in a loop around the supporting sleeve. At the other end of the cable there is a means 21 intended for hooking into a suitable engagement perforation 15, so that the cable is anchored and can be tensioned by pivoting the associated tensioning arm from its unlocked (swung out from the fastening plate) position to its locked tensioning position, in which the arm is swung to bear against the fastening plate 14. Tightening the tension cable about the supporting sleeve results in clamping the latter about the leg stump. In FIG. 2, 21' denotes the hooking means of the second tension cable 20', attached to the tensioning arm 17' by its cable eye 19'.

It should be noted here that clamping of the supporting bands 13 against the outside of the carrying sleeve halves is done most simply by the bands 13 being laid inside the cables 20,20' and the fastening plate 14. When the cables are tightened round the carrying sleeve, they very effectively lock the bands 13 against the outside of the sleeve halves.

Positioning the leg stump laterally in relation to the prosthesis takes place in the illustrated embodiment with the aid of a device comprising tension straps 22, intended for being tightened against opposite sides of the stump, in its supporting stocking and accommodated in the carrying sleeve. For this purpose, the tension straps 22 extend from an anchoring point, e.g. a pair of parallel slits, at the back plate 5, on either side of the stump, and out through a common, vertical slot 23 in the front plate 4. Depending on the individual length of the stump and the desired lateral inclination of the stump in the prosthesis, the tension straps 22 may need to be movable to alternative positions on the prosthesis. For this reason the latter is suitably provided with several anchoring points along the length of the back plate 5, as well as several slots 23 in a row, in the front plate 4.

The tension straps 22 are thus placed at a suitable point along the prosthesis and provide, when they are tensioned between the back anchoring point and the front slot, a lateral force on the leg stump, and thereby mutual fixation of the stump and the prosthesis.

FIG. 5 schematically illustrates how the tension straps 22 constitute parts of one and the same strap, and can be fixed and locked against a stump with the help of Velcro ® tape, i.e. releasable fastenings of the Velcro-tape type, such tape denoted 24a and 24b in the figure.

It will be seen from FIG. 4 that the backwardly directed side portions of the front plate sleeve half 7 and the forwardly directed side portions of the back plate sleeve half 8 have horizontal slots 25 and 26, respectively, dividing each of the side portions into two separate tongues. Adjacent tongues of the back and front sleeve halves are thus enabled to glide over each other, and the halves 7,8 can thus be pushed together or pulled apart in complementary registry.

The longitudinal fixation of the prosthesis relative to the stump is done, as will be seen from FIGS. 2 and 4, with the help of a tensionable band or strap 27 which is laid around the stump in the form of an upward loop in the region above the knee, and extends between the attachment points 28,29 on the opposing side portions of the back sleeve half 8.

Turning in conclusion to FIG. 1, it is pointed out that both plates 4 and 5 can suitably be provided with rows of fixing holes 30,31 to enable fitting the prosthetic foot 3 at a desired location when the plates 4,5 have been cut off to give the right length to the artificial lower leg.

What we claim is:

1. A prosthesis for replacing an amputated lower leg comprising a front plate and a back plate opposing the front plate, said plates having lower portions and upper portions and being rigidly joined to each other at their lower portions and adapted to be articulately connected at their lower portions to a prosthetic foot, the upper portion of each plate being shaped as a sleeve half and cooperating with the other sleeve half in a circular configuration to form an upward bowl-like enlarged carrying sleeve, the material of the plates being sufficiently spring-like to allow the upper portions of the plates to be resiliently pulled apart so that a leg stump can be inserted into the carrying sleeve; means for pulling the sleeve halves together so as to maintain a firm grip around a leg stump, means for laterally adjusting the prosthesis relative to a stump, and means for fixing the prosthesis longitudinally relative to a stump.

2. A prosthesis is claimed in claim 1, wherein the means for pulling together the sleeve halves comprises a fastening plate attached to the front of the front plate, said fastening plate having engagement openings and tensioning arms pivotably mounted at the ends of the fastening plate, a tension cable having one end pivotably mounted on each tensioning arm, said cable extending backwards from its tensioning arm in a loop around the carrying sleeve with hook means at the other end of the cable enabling anchorage of the cable in one of the engagement openings, whereby swinging each tensioning arm to its locked tensioned position results in tightening the associated cable about the carrying sleeve and thereby tightening the sleeve around a leg stump.

3. A prosthesis as claimed in claim 1 or 2, wherein the means for lateral positioning of the prosthesis comprises tightenable tension straps arranged below the sleeve and extending between the back and the front plate with lengths which can be adjusted between the plates.

4. A prosthesis as claimed in claim 1, wherein the backwardly directed side portions of the front plate sleeve half and/or the forwardly directed side portions of the back plate sleeve half have substantially horizontal slits forming the respective side portion into at least two separate tongues enabling the respective sleeve halves to be drawn together by the respective tongue being glidably displaceable on the adjacent side portion of the sleeve half.

5. A prosthesis as claimed in claim 1 wherein the means for longitudinally fixing the prosthesis relative to a leg stump comprises attachments fixed to opposing sides of either sleeve half, between which a strap or band is adjustably tensionable in the form of an upward loop, which can be so laid around the leg stump that at least the larger part of the loop surrounds the stump in the region above the knee.

6. A prosthesis as in claim 1 including a stocking adapted to be pulled over a leg stump, the stocking having supporting bands attached to the outside thereof and extending up along the stocking, the bands having free ends adapted to be folded downwardly over the edge of the carrying sleeve for clamping against the outside of the sleeve halves.

7. A prosthesis as in claim 6 including tension bands clamping the supporting bands against the outside of the sleeve halves.

8. A prosthesis as in claim 1 including a prosthetic foot articulately connected to the lower portions of said plates.

* * * * *